(12) United States Patent
Knevels et al.

(10) Patent No.: US 7,621,191 B2
(45) Date of Patent: Nov. 24, 2009

(54) IMMERSION PROBE

(75) Inventors: Johan Knevels, Bree (BE); Guido Cappa, Houthalen (BE); Jos Truyen, Eksel (BE); Jean Claes, Meeuwen (BE)

(73) Assignee: Heraeus Electro-Nite International N.V., Houthalen (BE)

( * ) Notice: Subject to any disclaimer, the term of this patent is extended or adjusted under 35 U.S.C. 154(b) by 228 days.

(21) Appl. No.: 11/530,205

(22) Filed: Sep. 8, 2006

(65) Prior Publication Data

US 2007/0056393 A1 Mar. 15, 2007

(30) Foreign Application Priority Data

Sep. 13, 2005 (DE) ........................ 10 2005 043 852

(51) Int. Cl.
*G01N 1/12* (2006.01)
(52) U.S. Cl. ....................... 73/864; 73/866.5; 73/DIG. 9
(58) Field of Classification Search ................ 73/64.56, 73/864.53, 864.59, 864.73, 866.5, DIG. 9
See application file for complete search history.

(56) References Cited

U.S. PATENT DOCUMENTS

| 3,091,969 A | 6/1963 | Romanchuk et al. |
| 5,011,279 A | * 4/1991 | Auweter et al. ............ 356/28.5 |
| 5,131,633 A | 7/1992 | Brinker |
| 5,411,103 A | 5/1995 | Werner |
| 5,435,196 A | 7/1995 | Cassidy |

FOREIGN PATENT DOCUMENTS

| DE | 32 33 677 C1 | 12/1983 |
| DE | 285190 | 12/1990 |
| FR | 2021890 A | 7/1970 |
| FR | 2546625 A1 | 11/1984 |
| GB | 1173849 | 12/1969 |
| GB | 1274618 | 5/1972 |
| JP | 49-24456 Y * | 7/1974 |
| JP | 55-14805 U * | 1/1980 |
| JP | 57080559 A | 5/1982 |
| JP | 11304669 A | 5/1999 |
| JP | 2002116199 A | 4/2002 |

* cited by examiner

*Primary Examiner*—Thomas P Noland
(74) *Attorney, Agent, or Firm*—Panitch Schwarze Belisario & Nadel LLP

(57) ABSTRACT

An immersion probe has a probe body having a longitudinal axis and an outer surface surrounding the longitudinal axis, wherein a portion of the outer surface has sampling elements, which extend around the longitudinal axis in the peripheral direction and which have a radial dimension. A protective layer, which can be dissolved or combusted in molten steel or slag, is arranged around the sampling elements.

19 Claims, 4 Drawing Sheets

IMMERSION PROBE

BACKGROUND OF THE INVENTION

The invention relates to an immersion probe comprising a probe body having a longitudinal axis and an outer surface surrounding the longitudinal axis, wherein one portion of the outer surface has sampling elements, which have a radial dimension and which extend around the longitudinal axis in the peripheral direction.

Such immersion probes are known from U.S. Pat. No. 5,435,196. Here, a probe is described for collecting slag samples. The probe body has a carrier tube, around which a ring structure composed of twisted wire is arranged. The ring structure is movable in the longitudinal direction. The slag arranged on the molten metal is to remain adhered to the ring structure when the probe is immersed in the molten metal. The slag can then be analyzed after pulling the probe out of the melt. Depending on the viscosity of the slag, the adhering quantity is more or less large, so that even under some circumstances, too little slag is available for an analysis.

Similar samplers are known from Japanese patent publications JP 14805/80 and JP 24456/74. In U.S. Pat. No. 5,131,633, a rod-shaped sampler is described, in which the slag sample is to remain adhered to the jacket surface of the rods.

BRIEF SUMMARY OF THE INVENTION

The invention is based on the object of improving the known immersion probes and enabling effective slag sampling. This object is achieved according to one embodiment of the invention in which an immersion probe includes a probe body having a longitudinal axis and an outer surface surrounding the longitudinal axis, wherein a portion of the outer surface has sampling elements, which extend around the longitudinal axis in the peripheral direction and which have a radial dimension, is characterized by a protective layer, which can be dissolved or combusted in the molten steel or slag, arranged around the sampling elements.

Because a protective layer, which can be dissolved or combusted in molten steel or slag, is arranged around the sampling elements, the slag layer lying, for example, on molten steel, thereby reaches the sampling element only after a certain delay. In this way, it has been surprisingly shown that just by these means, a sufficient amount of slag is captured and thus a sufficiently large sample can be made available for analysis. The protective layer prevents the molten slag from reaching the sampling elements too quickly and from damaging these elements, before the probe body is pulled out of the molten slag. In particular, this has proven to be advantageous in immersion probes, which contain additional sensors and/or sample chambers, because the following measurement or sampling therewith lasts a few seconds longer than the removal of the slag sample.

The protective layer is preferably made of cardboard or paper. In particular, it can have a tubular shape. The sampling elements can have a flat or concave surface facing away from the immersion end of the probe body. Here, the flat or concave profile should extend in the radial direction. The sampling elements can be formed as disks running around the longitudinal axis or in the form of a spiral made of a band wound around the longitudinal axis. The flat or concave surface can be inclined to the longitudinal axis in the direction of the end of the probe body opposite the immersion end. The angle formed here between this surface and the longitudinal axis can advantageously amount to approximately between 45° and 90°.

Upon immersion or after the protective layer dissolves, slag flows onto these sampling elements, adheres there, and then can be removed after the immersion probe is pulled out of the melt. For this purpose, the sampling elements are pressed together, so that the slag falls off. It is then granulated and fed to the analysis device.

Preferably, the sampling elements are made of steel, which has a wall thickness that can be less than 1 mm. The sampling elements are advantageously formed as a separate part of the probe body and comprise a different material than the remaining parts of the probe body, thus, for example, made of steel, while the other part of the probe body can be made of cardboard. The probe body preferably has a tubular shape. At least one sensor or a sampler for molten metal can be arranged on or in the probe body. It is possible to form the sampling elements as one or more ring elements arranged one behind the other in the direction of the longitudinal axis, whereby an easier assembly is possible.

A second embodiment of the invention is characterized by the sampling elements having a flat or concave surface facing away from an immersion end of the probe body. This surface is inclined relative to the longitudinal axis in the direction of the end of the probe body opposite the immersion end. The sampling elements for this embodiment can also be made preferably of steel, they can be formed as a separate part of the probe body made of a different material than the other part of the probe body, and they can be formed, in particular, as one or more ring elements arranged one behind the other in the direction of the longitudinal axis. The remaining part of the probe body can be made of cardboard, wherein in this embodiment also the probe body preferably has a tubular shape.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
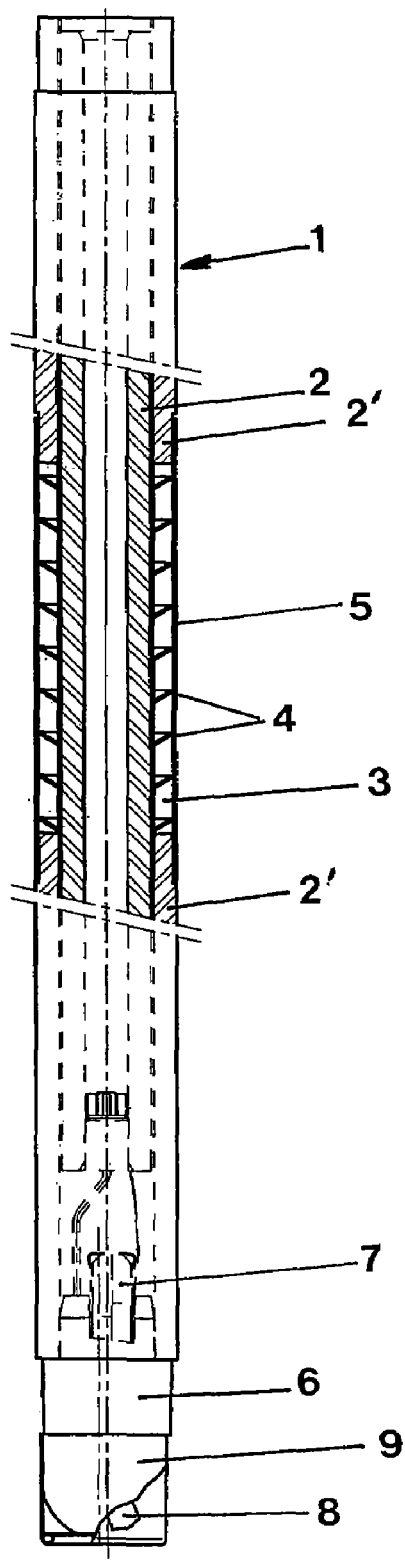
FIG. 1 is a schematic, longitudinal sectional view, partially broken away, of an immersion probe according to one embodiment of the invention.

The immersion probe has a probe body 1, which is formed from two cardboard tubes 2; 2' fixed one over the other. The outer cardboard tube 2' is composed of two parts, which are arranged one behind the other in the longitudinal direction and which have a spacing between them, so that a wide groove 3 is created on the periphery of the probe body 1. In this groove 3 there are sampling elements 4. The sampling elements 4 are formed as flat rings, which are angled upwardly, so that slag can collect in them. Around the sampling elements 4 there is a 1 to 5 mm thick protective layer 5 made of cardboard. The protective layer 5 dissolves when the immersion probe is immersed into the melt, so that slag reaches the sampling elements 4 and remains adhered there.

The probe body 1 has an immersion end, on which an immersion head 6 is arranged. In the immersion head 6 there is a sample chamber 7 for removing samples of the molten steel arranged under the slag layer. The molten steel flows through an inlet tube 8 into the sample chamber 7. The opening of the inlet tube 8 is protected by a cardboard cap 9. This cardboard cap 9 leaves the inlet opening of the inlet tube 8 open to the molten steel.

Figure 2:
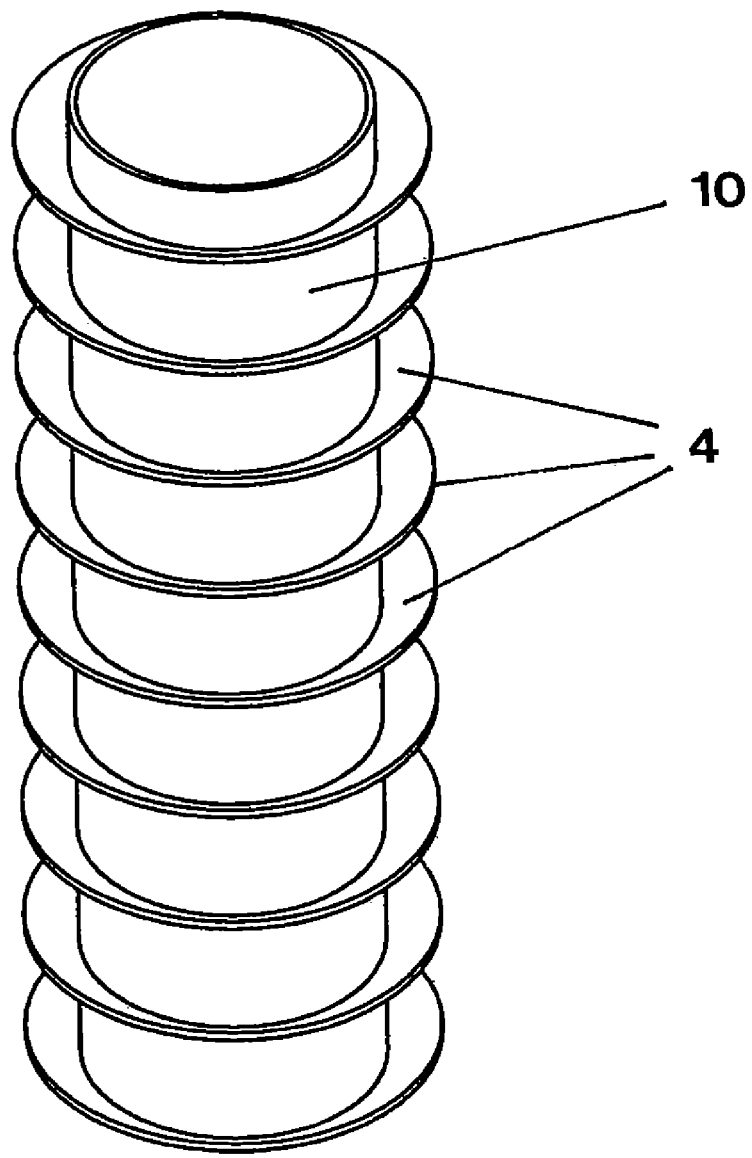
FIG. 2 is a perspective, detail view of a sampling element according to one embodiment of an immersion probe of the invention.

In FIG. 2 the sampling elements 4 are shown. These are arranged in a ring shape one behind the other on a steel tube 10. The sampling elements 4 themselves are likewise made of steel. The thickness (wall thickness) of the sampling elements 4 and the steel tube 10 amounts to approximately 1 mm or even less. The sampling elements 4 are angled upwardly, that is, opposite to the immersion direction. They form an angle of approximately 60° with the longitudinal axis of the probe body 1.

Figure 3:
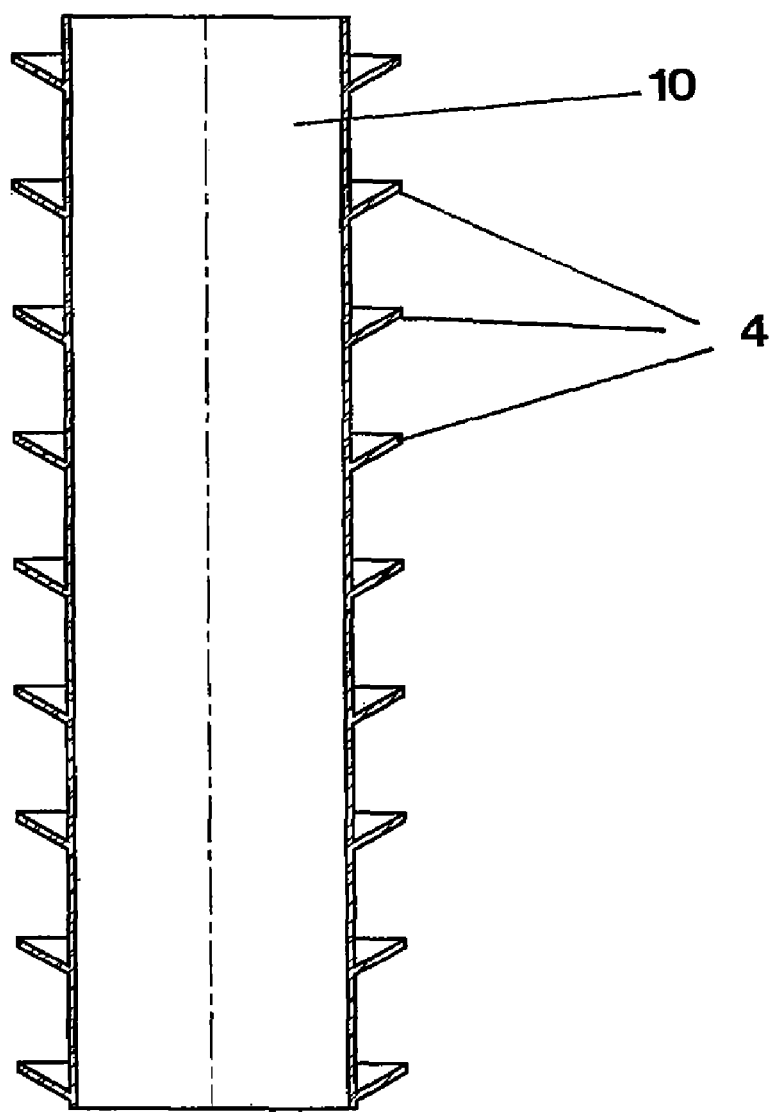
FIG. 3 is a longitudinal sectional view of the sampling element of FIG. 2.

After the sampling the probe body 1 is pulled out of the melt. A radial pressure is exerted on the sampling elements 4, so that these are crushed. In this way, the very brittle slag falls from the sampling elements in a coarse-grained form. The slag is reduced in size and fed to an analysis device. FIG. 3 shows the sampling elements 4 in section.

Figure 4:
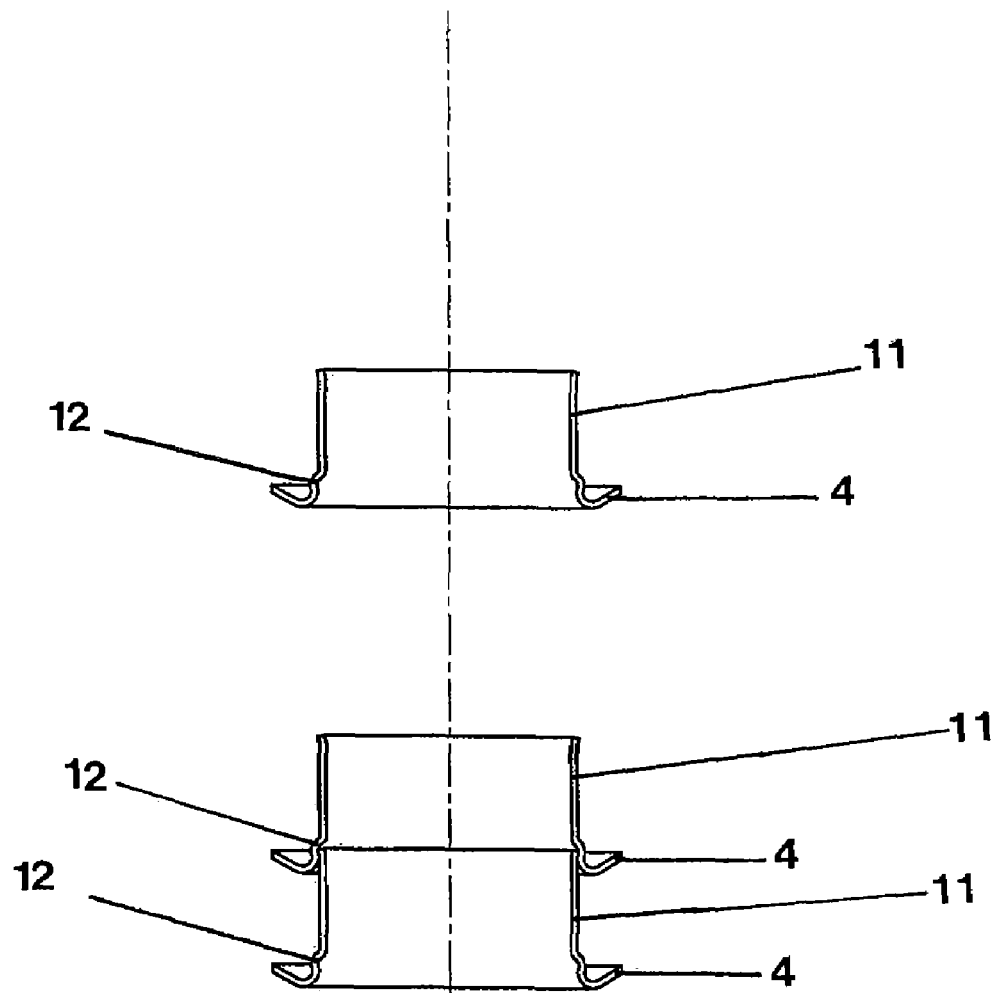
FIG. 4 is and exploded, longitudinal sectional view of another possible construction of a sampling element according to an embodiment of an immersion probe of the invention.

FIG. 4 shows another possible construction of the sampling elements 4. The sampling elements 4 are formed as annular flat rings as the bottom part of a relatively short metal sleeve 11, whereby the elements 4 are created by bending back the metal sleeve 11. An annular groove 12 is created at the bending point. This groove 12 is set on the top edge of a metal sleeve 11 placed underneath, so that by stacking several segments, a sampling body similar to the one shown in FIGS. 2 and 3 is created.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. An immersion probe comprising a probe body having a longitudinal axis, an outer surface surrounding the longitudinal axis and an immersion end, a portion of the outer surface having sampling elements, the sampling elements extending around the longitudinal axis in a peripheral direction and having a radial dimension, wherein the sampling elements are formed as a separate part of the probe body and comprise a different material than a remaining part of the probe body, and wherein the sampling elements have a flat or concave surface, which faces away from the immersion end, the flat or concave surface being inclined relative to the longitudinal axis in a direction of the end of the probe body opposite the immersion end.

2. The immersion probe according to claim 1, wherein the sampling elements comprise steel.

3. The immersion probe according to claim 1, wherein the remaining part of the probe body comprises cardboard.

4. The immersion probe according to claim 1, further comprising a protective layer, dissolvable or combustible in a molten bath, arranged around the sampling elements.

5. The immersion probe according to claim 4, wherein the protective layer comprises cardboard or paper.

6. The immersion probe according to claim 4, wherein the protective layer has a tubular shape.

7. The immersion probe according to claim 1, wherein at least one sensor or one sample chamber is arranged on or in the probe body.

8. An immersion probe comprising a probe body having a longitudinal axis, an outer surface surrounding the longitudinal axis and an immersion end, a portion of the outer surface having sampling elements, the sampling elements extending around the longitudinal axis in a peripheral direction and having a radial dimension, wherein the sampling elements are formed as one or more ring elements arranged one behind another in a direction of the longitudinal axis, and wherein the sampling elements have a flat or concave surface, which faces away from the immersion end, the flat or concave surface being inclined relative to the longitudinal axis in a direction of the end of the probe body opposite the immersion end.

9. The immersion probe according to claim 8, wherein the sampling elements comprise steel.

10. The immersion probe according to claim 8, further comprising a protective layer, dissolvable or combustible in a molten bath, arranged around the sampling elements.

11. The immersion probe according to claim 10, wherein the protective layer comprises cardboard or paper.

12. The immersion probe according to claim 10, wherein the protective layer has a tubular shape.

13. The immersion probe according to claim 8, wherein at least one sensor or one sample chamber is arranged on or in the probe body.

14. An immersion probe comprising a probe body having a longitudinal axis, an outer surface surrounding the longitudinal axis and an immersion end, the probe body having a tubular shape and a portion of the outer surface having sampling elements, the sampling elements extending around the longitudinal axis in a peripheral direction and having a radial dimension, wherein the sampling elements have a flat or concave surface, which faces away from the immersion end, and wherein the flat or concave surface is inclined relative to the longitudinal axis in a direction of the end of the probe body opposite the immersion end.

15. The immersion probe according to claim 14, wherein the sampling elements comprise steel.

16. The immersion probe according to claim 14, further comprising a protective layer, dissolvable or combustible in a molten bath, arranged around the sampling elements.

17. The immersion probe according to claim 16, wherein the protective layer comprises cardboard or paper.

18. The immersion probe according to claim 16, wherein the protective layer has a tubular shape.

19. The immersion probe according to claim 14, wherein at least one sensor or one sample chamber is arranged on or in the probe body.

* * * * *

UNITED STATES PATENT AND TRADEMARK OFFICE
CERTIFICATE OF CORRECTION

PATENT NO. : 7,621,191 B2 Page 1 of 1
APPLICATION NO. : 11/530205
DATED : November 24, 2009
INVENTOR(S) : Knevels et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 305 days.

Signed and Sealed this

Twenty-sixth Day of October, 2010

David J. Kappos
*Director of the United States Patent and Trademark Office*